United States Patent
Kroenke et al.

(10) Patent No.: US 12,148,201 B2
(45) Date of Patent: Nov. 19, 2024

(54) CONSTRAINED TRAINING OF ARTIFICIAL NEURAL NETWORKS USING LABELLED MEDICAL DATA OF MIXED QUALITY

(71) Applicant: KONINKLIJKE PHILIPS N.V., Eindhoven (NL)

(72) Inventors: Sven Kroenke, Hamburg (DE); Jens Von Berg, Hamburg (DE); Daniel Bystrov, Hamburg (DE); Bernd Lundt, Hamburg (DE); Nataly Wieberneit, Hamburg (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 374 days.

(21) Appl. No.: 17/776,083

(22) PCT Filed: Nov. 9, 2020

(86) PCT No.: PCT/EP2020/081434
§ 371 (c)(1),
(2) Date: May 11, 2022

(87) PCT Pub. No.: WO2021/094238
PCT Pub. Date: May 20, 2021

(65) Prior Publication Data
US 2022/0392198 A1 Dec. 8, 2022

(30) Foreign Application Priority Data
Nov. 14, 2019 (EP) .................................... 19209033

(51) Int. Cl.
*G06V 10/774* (2022.01)
*G06T 7/00* (2017.01)
(Continued)

(52) U.S. Cl.
CPC .......... *G06V 10/774* (2022.01); *G06T 7/0012* (2013.01); *G06V 10/776* (2022.01);
(Continued)

(58) Field of Classification Search
CPC .. G06V 10/82; G06V 10/764; G06V 2201/03; G06V 10/25; G06V 10/454;
(Continued)

(56) References Cited

U.S. PATENT DOCUMENTS

2006/0085188 A1* 4/2006 Goodwin ............... G11B 27/28
704/E15.005
2008/0175476 A1* 7/2008 Ohk ........................ H04N 1/41
382/176
(Continued)

FOREIGN PATENT DOCUMENTS

WO WO2017191248 A1 11/2017

OTHER PUBLICATIONS

PCT International Search Report, International application No. PCT/EP2020/081434, Jan. 21, 2021.
(Continued)

*Primary Examiner* — Ajibola A Akinyemi
(74) *Attorney, Agent, or Firm* — Larry Liberchuk (57) ABSTRACT

The invention relates to a method (100) for supervised training of an artificial neural network for medical image analysis. The method comprises acquiring (S1) first and second sets of training samples, wherein the training samples comprise feature vectors and associated predetermined labels, the feature vectors being indicative of medical images and the labels pertaining to anatomy detection, to semantic segmentation of medical images, to classification of medical images, to computer-aided diagnosis, to detection and/or localization of biomarkers or to quality assessment of medical images. The accuracy of predetermined labels may
(Continued)

be better for the second set of training samples than for the first set of training samples. The neural network is trained (S3) by reducing a cost function, which comprises a first and a second part. The first part of the cost function depends on the first set of training samples, and the second part of the cost function depends on a first subset of training samples, the first subset being a subset of the second set of training samples. In addition, the second part of the cost function depends on an upper bound for the average prediction performance of the neural network for the first subset of training samples and the second part of the cost function is configured for preventing that the average prediction performance for the first subset of training samples exceeds the upper bound.

14 Claims, 2 Drawing Sheets

(51) Int. Cl.
*G06V 10/776* (2022.01)
*G06V 10/82* (2022.01)
*G16H 30/40* (2018.01)

(52) U.S. Cl.
CPC .............. *G06V 10/82* (2022.01); *G16H 30/40* (2018.01); *G06T 2207/20081* (2013.01); *G06T 2207/20084* (2013.01); *G06V 2201/03* (2022.01)

(58) Field of Classification Search
CPC ........... G06V 40/171; G06V 30/19173; G06V 30/194; G06V 10/225; G06V 10/774; G06V 20/49; G06V 40/103; G06V 20/56; G06V 20/46; G06V 20/588
USPC .......................................................... 382/128
See application file for complete search history.

(56) References Cited

U.S. PATENT DOCUMENTS

| | | | |
|---|---|---|---|
| 2009/0248608 A1* | 10/2009 | Ravikumar | ......... G06F 16/9577 706/55 |
| 2014/0180975 A1 | 6/2014 | Martinez | |
| 2014/0307958 A1 | 10/2014 | Wang | |
| 2016/0117587 A1 | 4/2016 | Yan | |

OTHER PUBLICATIONS

Prechelt L. et al., "Automatic Early Stopping Using Cross Validation: Quantifying the Criteria", Neural Networks, ELS EV I ER Science Publishers, Barking, GB, vol. 11, No. 4, Jun. 1, 1998 (Jun. 1, 1998), pages 761-767, XP004146675.

Perez L. et al., "The Effectiveness of Data Augmentation in Image Classification Using Deep Learning", Computer Science, Computer Vision and Pattern Recognition (cs.CV), arXiv:1712.04621 (2017).

Kamnitsas K. et al., "Unsupervised Domain Adaptation in Brain Lesion Segmentation with Adversarial Networks", Computer Science, Computer Vision and Pattern Recognition (cs.CV), arXiv:1612.08894 (2016).

Paul S. et al., "Inter-Radiologist Concordance in Pulmonary Tuberculosis vs. Normal Chest X-Ray Classification to Arrive at Expected Performance Level of Automated Classification", Electronic Poster C-2197, ECR 2018.

* cited by examiner

CONSTRAINED TRAINING OF ARTIFICIAL NEURAL NETWORKS USING LABELLED MEDICAL DATA OF MIXED QUALITY

FIELD OF THE INVENTION

The invention relates to a computer-implemented method for supervised training of an artificial neural network using labelled medical images of mixed quality, a data processing system configured to carry out the steps of this method, a computer program comprising instructions to cause the data processing system to execute the method, and a computer-readable medium having stored such computer program.

BACKGROUND OF THE INVENTION

The supervised training of neural networks, in particular of deep neural networks, is known to require extensive sets of training samples. Using training sets of insufficient size leads to a high risk of generalization errors when applying the trained neural network to new, unseen cases. Despite of recent progress in training on synthetic or synthetically augmented data as well as in data domain transfer techniques, a sufficiently broad variability within the training data is typically a precondition for a good generalizability of the neural network, which means in practice a massive amount of data.

Supervised training of a neural network is, e.g., disclosed in the article "Automatic early stopping using cross validation: quantifying the criteria" by L. Prechelt in Neural Networks 11 (1998), 761-767. This article also describes how overfitting can be avoided by stopping the training before convergence. This is done by splitting the training data into a training set and a cross validation set and training only the training set and evaluating the per-example error on the validation set once in a while. The training is stopped as soon as the error on the cross validation set is higher than it was the last time.

Besides the bare number of the training samples, also the label quality plays an important role for the prediction accuracy of the trained neural network. While a certain degree of errors in the labels can be tolerated, and can even improve the generalization performance, the prediction accuracy of the trained neural network degrades drastically if the number of inaccurately or incompletely labelled training samples is too large. The latter situation must in particular be avoided for medical applications where the highest accuracy, robustness and reliability criteria apply.

SUMMARY OF THE INVENTION

Accurately labelling medical images requires an enormous amount of resources, in particular medical expertise, time, and money. Hence, one can typically not obtain sufficiently many training samples with high label quality. This holds in particular for tasks with a high degree of inter- and intra-reader variability, where a certain form of consensus has to be achieved among different readers, or the same reader but multiple readings of the same image. Mostly, the available resources allow for accurately labelling only a certain fraction of the available medical images while the remaining, much larger fraction has to be labelled by less experienced staff, which usually leads to inaccurate and possibly incomplete labels.

In such a setting, training a neural network on all training samples without singling out training samples with high-quality labels may result in a poor prediction accuracy of the trained neural network. This may be circumvented to a certain degree by drawing training samples from the two label-quality categories in a more balanced way during training. Yet the latter approach suffers from the drawback that the performance of the neural network on the training samples with high-quality labels is not explicitly controlled.

It may therefore be desirable to provide an improved method for training an artificial neural network. In particular, the method may better utilize the available training samples of mixed label quality, providing an explicit control of the accuracy on the training samples with high-quality labels. Thereby, the prediction accuracy of the trained neural network may be improved.

This is achieved by the subject matter of the independent claims, wherein further embodiments are incorporated in the dependent claims and the following description. It should be noted that any step, feature or aspect of the computer-implemented method, as described in the following, equally applies to the data processing system configured to carry out the steps of the method, the computer program, and the computer readable medium, as described in the following, and vice versa.

According to a first aspect of the present disclosure, a computer-implemented method for supervised training of an artificial neural network is presented, wherein the neural network is configured for medical image analysis. The neural network is further configured to predict a label based on a feature vector indicative of a medical image. The computer-implemented method comprises acquiring first and second sets of training samples, wherein the training samples comprise feature vectors and associated predetermined labels, the feature vectors being indicative of medical images and the labels pertaining to anatomy detection, to semantic segmentation of medical images, to classification of medical images, to computer-aided diagnosis, to detection and/or localization of biomarkers or to quality assessment of medical images. Furthermore, the computer-implemented method comprises acquiring an upper bound for an average prediction performance of the neural network for a first subset of training samples, the first subset being a subset of the second set of training samples. Moreover, the computer-implemented method comprises training the neural network by reducing a cost function, wherein the cost function comprises a first part and a second part, wherein the first part of the cost function depends on the first set of training samples, and wherein the second part of the cost function depends on the first subset of training samples and the upper bound for the average prediction performance of the neural network for the first subset of training samples. The second part of the cost function is configured for preventing that the average prediction performance for the first subset of training samples exceeds the upper bound.

The computer-implemented method is beneficial in particular for deep neural networks, which comprise numerous parameters to be learned. Typically, the required number of training samples increases with increasing numbers of parameters that need to be learned. The neural network may be described by a function $\hat{y}=F(x; w)$, where x denotes the feature vector indicative of a medical image, w denotes a weight vector, and $\hat{y}$ is the label predicted by the neural network. The feature vector may comprise raw image data. Additionally or alternatively, the feature vector may comprise features derived from the raw image data. The neural network is parameterized by the weight vector w, which is to be learned by training the neural network. The predicted label may be a number and/or a string. Alternatively, the predicted label may comprise a plurality of numbers and/or strings. The numbers and/or strings may correspond to the entire medical image or to a section of the image. It is also possible that the predicted label comprises one or more numbers and/or one or more strings for a pixel of the medical image. In particular, the predicted label may comprise one or more numbers and/or one or more strings for each pixel of the medical image.

Preferably, each training sample of the first and second sets of training samples comprises a feature vector x indicative of a medical image and an associated predetermined label y. Hence, each training sample may be a tuple (x, y). The predetermined labels may be determined manually, and may be considered as a ground truth for the training of the neural network. The first and second sets of training samples may be acquired, for example, by loading these sets from a computer readable storage medium or by downloading these sets from a remote server.

The average accuracy of the predetermined labels or the confidence in these labels may be better for the second set of training samples than for the first set of training samples. Thereby, the accuracy of a predetermined label y is a measure for the deviation of y from the corresponding exact label y*. Additionally or alternatively, an accurate prediction of labels may be considered more important for the second set of training samples than for the first set of training samples. For example, the second set of training samples may correspond to images showing a disorder such as a bleeding or a disease, whereas the first set of training samples may correspond to images not showing such a disorder. It may be considered important that the false negative rate is small, i.e. that the probability of not detecting an existing disorder is small. At the same time, false positives may be less critical. Hence, it may be desirable to have an accurate prediction of labels in particular for the second set of training samples.

Training the neural network may be accomplished by reducing a cost function with respect to the weight vector w of the neural network. Hence, the cost function may be a function of the weight vector of the neural network, and the neural network may be trained by searching for the weight vector, which minimizes the cost function. The cost function is parameterized by training samples. The cost function may be the sum of a first part and a second part.

The first part of the cost function depends on the first set of training samples. The first part of the cost function may be based on a first label prediction error measure $A_1(y, \hat{y})=A_1(y, F(x; w))$, which may be evaluated for training samples of the first set of training samples. The first label prediction error measure $A_1(y, \hat{y})$ may be a measure for a deviation between the predetermined label y of a training sample and the label $\hat{y}$ predicted by the neural network based on the feature vector x of the training sample. For example, the first part of the cost function may be or may be based on the average of first label prediction error measures $A_1(y, \hat{y})$ for the first set of training samples. Hence, the first part of the cost function may be based on the average prediction performance for the first set of training samples, measured by means of the first label prediction error measure $A_1(y, \hat{y})$. The first label prediction error measure is preferably differentiable almost everywhere. Moreover, the norm of the gradient of $A_1(y, F(x; w))$ with respect to w is preferably large when F(x; w) strongly deviates from y.

The second part of the cost function depends on the first subset of training samples. Hence, the first subset comprises training samples (x, y), which are also contained in the second set of training samples. The first subset may be a proper subset of the second set of training samples, or the first subset may be equal to the second set of training samples. The second part of the cost function may be based on a second label prediction error measure $A_2(y, \hat{y})=A_2(y, F(x; w))$, which may be evaluated for training samples of the first subset of training samples. The second label prediction error measure $A_2(y, \hat{y})$ may be a measure for a deviation between the predetermined label y of a training sample and the label $\hat{y}$ predicted by the neural network based on the feature vector x of the training sample. For example, the second part of the cost function may be or may be based on the average of second label prediction error measures $A_2(y, \hat{y})$ for the first subset of training samples. Hence, the second part of the cost function may be based on the average prediction performance for the first subset of training samples, measured by means of the second label prediction error measure $A_2(y, \hat{y})$. The second label prediction error measure is preferably differentiable almost everywhere. Moreover, the norm of the gradient of $A_2(y, F(x; w))$ with respect to w is preferably large when F(x; w) strongly deviates from y.

The first and second label prediction error measures may be identical, but it is also possible that different label prediction error measures are used for the first and second parts of the cost function. For example, the first label prediction error measure may be based on the cross entropy function, whereas the second label prediction error measure may be based on the soft-dice loss function.

The average prediction performance of the neural network for the first subset of training samples is preferably the average of label prediction error measures $A_2(y, \hat{y})=A_2(y, F(x; w))$ for the first subset of training samples. The upper bound for the average prediction performance of the neural network for the first subset of training samples may be determined intuitively by a user. This may be possible in particular when values of the second label prediction error measure $A_2(y, \hat{y})$ can be interpreted intuitively. Alternatively, the upper bound for the average predication performance for the first subset of training samples may be based on a regulatory specification. Furthermore, the second set of training samples may be based on a regulatory specification. The upper bound may be an input provided by a user upon a request from a data processing system, it may be loaded from a computer readable storage medium, or it may be downloaded from a remote server. Alternatively, the upper bound for the average prediction performance of the neural network for the first subset of training samples may be determined automatically or semi-automatically. For example, the neural network may be pre-trained using a pre-training set of training samples. The pre-training set of training samples may be another subset of the second set of training samples. Preferably, the pre-training set of training samples and the first subset of training samples are disjoint. The average prediction performance of the pre-trained neural network may then be determined for the first subset of training samples using the second label prediction error measure $A_2(y, \hat{y})$. This average prediction performance may be or may be utilized for determining the upper bound for the average predication performance of the neural network for the first subset of training samples.

The second part of the cost function depends on the upper bound for the average prediction performance of the neural network for the first subset of training samples. The second part of the cost function may be configured such that it increases sharply when the average prediction performance for the first subset of training samples exceeds the upper bound. Hence, the second part of the cost function is configured for preventing that the average prediction performance for the first subset of training samples exceeds the upper bound.

Moreover, the second part of the cost function may be set to zero when the average prediction performance of the neural network for the first subset of training samples does not exceed the upper bound. The second part of the cost function may therefore be configured to prevent that minimizing the cost function leads to an overfitting of the weights of the neural network to the training samples of the first subset of training samples.

The neural network is configured for medical image analysis. In particular, the neural network may be configured for anatomy detection, for semantic segmentation of medical images, for classification of medical images, for computer-aided diagnosis, for detection and/or localization of biomarkers, or for quality assessment of medical images.

Hence, in an example, the neural network is configured for computer-aided diagnosis. In particular, the neural network may be configured for detecting and/or classifying lung nodules in computed tomography (CT) images. The first set of training samples may be constructed from chest CT images and corresponding annotations extracted from reports of the clinical routine. The second set of training samples may be constructed by considering only cases where a biopsy has confirmed the lung-nodule detection and/or classification of a radiologist. Hence, the labels of the training samples of the second set of training samples may be more reliable as compared to the labels of the training samples of the first set of training samples. The second label prediction error measure may be the soft-dice loss function of the predicted nodule bounding box. Then, the upper bound for the average prediction performance of the neural network for the first subset of training samples may correspond to the maximally allowed location error of confirmed lung nodules.

Since training a neural network for, for example, detecting and/or classifying lung nodules in CT images may require huge amounts of training samples, an already trained neural network may be deployed to a clinic, and the neural network may be further improved by online learning on images read by in-house radiologists of the clinic in combination with annotations of nodules from reports of the clinic. With traditional neural network training methods, the online learning bears the risk that the prediction performance of the neural network successively degrades due to overfitting. In order to mitigate this risk, the method according to the invention may be applied. Thereby, the weight vector of the neural network may be updated when new training samples become available. Hence, the first and/or second sets of training samples may be extended over time. The first subset of training samples may be kept fixed, and the method for training the neural network may ensure that the average prediction performance over the fixed first subset of training samples does not degrade when the first and/or second sets of training samples are extended. Hence, the method for training the neural network may allow to explicitly control the average prediction performance for a fixed subset of training samples, which preferably comprises accurate predetermined labels.

Computer-aided diagnosis is often highly challenging, since it is difficult to obtain training samples with accurate predetermined labels. For example, detecting tuberculosis in chest X-ray images can be challenging for radiologists, in particular for less experienced ones. Letting multiple readers annotate the same set of images typically leads to a high inter-reader variance in the annotations, which makes it difficult to use them for training neural networks. In this situation, the second set of training samples may comprise training samples, for which multiple or all readers provided a consistent predetermined label. Additionally or alternatively, the second set of training samples may comprise training samples provided by a highly trained and experienced expert. The first set of training samples may comprise training samples provided by less experienced readers.

In another example, the neural network may be configured for the segmentation of complex anatomical structures. Generating training samples for training a neural network for semantic segmentation of medical images may be time-consuming and expensive, in particular when the target anatomies have to be labelled voxel-wise. Generating training samples may be complex, time-consuming and expensive for the following reasons: First, the anatomy of interest may have a complex geometry with many tiny but important details, which may hinder automatic assistance of the annotation procedure. An example for such an anatomy is the intestine in magnetic resonance (MR) images, where annotating all the windings and folds of the intestine may be quite laborious. Second, it may be hard to identify the anatomy in the image unless one is highly experienced. Such situations often occur in the context of X-ray imaging, where anatomical structures overlap in the projection, for example with bones constituting the wrist. Hence, quite some experience and anatomical knowledge may be required for disentangling the overlaying structures. The first set of training samples may be obtained by applying a traditional automatic segmentation algorithm (e.g. model-based-segmentation). The second set of training samples may be constructed by manual annotations or by manual corrections of training samples provided by a traditional automatic segmentation algorithm.

In another example, the second part of the cost function depends on a difference between the average prediction performance for the first subset of training samples and the upper bound for the average prediction performance for the first subset of training samples.

Hence, the cost function may be expressed as $c(w) = c_1(w) + c_2(\overline{A}_2(w) - \varepsilon)$, where $c_1(w)$ is the first part of the cost function, $c_2(\overline{A}_2(w) - \varepsilon)$ is the second part of the cost function, $\overline{A}_2(w)$ is the average prediction performance for the first subset of training samples, and $\varepsilon$ is the upper bound for the average prediction performance for the first subset of training samples. In particular, $\overline{A}_2(w)$ may be the average of the second label prediction error measures for the first subset of training samples.

In a simple case, the second part of the cost function may be given by $c_2(\overline{A}_2(w) - \varepsilon) = \overline{A}_2(w) - \varepsilon$ when $\overline{A}_2(w) > \varepsilon$ and $c_2(\overline{A}_2(w) - \varepsilon) = 0$ otherwise. Hence, values of $\overline{A}_2(w) > \varepsilon$ may be penalized, whereas values of $\overline{A}_2(w) \leq \varepsilon$ may be considered uncritical. By choosing $\varepsilon$ large enough, an overfitting of the neural network to the first subset of training samples may be prevented.

In another example, the second part of the cost function further depends on a positive weight.

For example, the second part of the cost function may be given by $c_2(\overline{A}_2(w) - \varepsilon) = \lambda(\overline{A}_2(w) - \varepsilon)$ when $\overline{A}_2(w) > \varepsilon$ and $c_2(\overline{A}_2(w) - \varepsilon) = 0$ otherwise. Thereby, $\lambda$ is a positive weight. Hence, the cost function may correspond to the Lagrangian of an optimization problem, which minimizes $c_1(w)$ subject to the constraint that $\overline{A}_2(w) \leq \varepsilon$.

Increasing the weight $\lambda$ may induce a stronger penalty for values of $\overline{A}_2(w)$ that are larger than $\varepsilon$. For a first weight $\lambda$, minimizing or reducing the cost function may result in an unacceptably large value of $\overline{A}_2(w)$. In such a case, the minimization or reduction of the cost function may be repeated using a second weight $\lambda$, which may be larger than the first weight, and which may result in a smaller value of $\overline{A}_2(w)$. Moreover, the weight $\lambda$ may be increased iteratively until the average prediction performance for the first subset of training samples is acceptable. For example, the weight $\lambda$ may be increased iteratively until the average prediction performance for the first subset of training samples is better than a threshold performance, which may be or may be based on the upper bound $\varepsilon$ for the average prediction performance for the first subset of training samples.

In another example, the second part of the cost function depends on a power of the difference between the average prediction performance for the first subset of training samples and the upper bound for the average prediction performance for the first subset of training samples, wherein the power may be strictly greater than one.

For example, the second part of the cost function may be given by $c_2(\overline{A}_2(w)-\varepsilon)=\lambda(\overline{A}_2(w)-\varepsilon)^p$ when $\overline{A}_2(w)>\varepsilon$ and $c_2(\overline{A}_2(w)-\varepsilon)=0$ otherwise. Thereby, the power p may be strictly greater than one. By choosing a power p strictly greater than one, the penalty for positive values of $\overline{A}_2(w)-\varepsilon$ that are smaller than one is reduced. Since the upper bound e for the average prediction performance for the first subset of the training samples may be based on a rough estimation, choosing a power strictly greater than one may provide an increased robustness against an improper choice of the upper bound $\varepsilon$. At the same time, choosing a power p strictly greater than one results in an increased penalty for values of $\overline{A}_2(w)-\varepsilon$ that are greater than one. Consequently, a power p>1 may be utilized for preventing large positive values of $\overline{A}_2(w)-\varepsilon$.

In another example, the second part of the cost function comprises a polynomial or piece-wise polynomial function of the difference between the average prediction performance for the first subset of training samples and the upper bound for the average prediction performance for the first subset of training samples. For example, the second part of the cost function may be zero when $\overline{A}_2(w)\leq\varepsilon$, and, when $\overline{A}_2(w)>\varepsilon$, it may comprise linear and quadratic terms of the difference between the average prediction performance for the first subset of training samples and the upper bound for the average prediction performance for the first subset of training samples. Thereby, small as well as large positive values of $\overline{A}_2(w)-\varepsilon$ may be penalized strongly. As a result, an acceptable value of $\overline{A}_2(w)$ may be achieved using few iterations over the weight $\lambda$. Hence, the computational complexity may be reduced, which may facilitate neural networks of larger depths. Preferably, the second part of the cost function is positive semi-definite function of the difference between the average prediction performance for the first subset of training samples and the upper bound for the average prediction performance for the first subset of training samples.

In another example, the first part of the cost function is based on a first label prediction error measure, the second part of the cost function is based on a second label prediction error measure, and the first and second label prediction error measures are not affine functions of each other.

For example, the second label prediction error measure may be selected such that the upper bound for the average prediction performance of the neural network for the first subset of training samples can be determined intuitively. For example, for a semantic image segmentation application, the second label prediction error measure may be based on the soft-dice loss function.

In contrast, the first label prediction error measure may be selected such that the method for training the neural network is robust against large errors in the predetermined labels of the first set of training samples. Additionally or alternatively, the first label prediction error measure may be selected such that the first part of the cost function or its gradient with respect to the weight vector w can be evaluated in a computationally efficient manner. For example, for a semantic image segmentation application, the first label prediction error measure may be based on the cross entropy function.

The first and second label prediction error measures are not affine functions of each other. In particular, the first and second label prediction error measures are not scaled versions of each other.

In another example, the first part of the cost function further depends on a second subset of training samples from the second set of training samples.

The second subset of training samples may be a proper subset of the second set of training samples, or the second subset may be identical with the second set of training samples. The first and second subsets of training samples may be disjoint, or these subsets may intersect at one or more training samples. In particular, the first and second subsets of training samples may be identical. A dependence of the first part of the cost function on the second subset of training samples may be beneficial, as it may provide a penalization of label prediction errors for training samples of the second set of training samples even when $\overline{A}_2(w)<\varepsilon$, i.e., when the average prediction performance for the first subset of training samples is smaller than the upper bound $\varepsilon$.

In another example, the cost function is reduced iteratively using a gradient descent algorithm, wherein an iteration comprises drawing a first mini-batch from the first set of training samples and computing an approximate gradient of the first part of the cost function based on the first mini-batch, and/or wherein the iteration comprises drawing a second mini-batch from the first subset of training samples, and computing an approximate gradient of the second part of the cost function based on the second mini-batch.

The cardinalities of the sets of training samples may be huge, in particular that of the first set of training samples. Hence, applying a gradient descent method, a steepest descent method, or Newton's method for reducing the cost function with respect to the weight vector w may result in a prohibitively high computational complexity. To reduce the computational complexity, a stochastic optimization method may be applied. For example, a stochastic gradient descent method may be applied. Hence, the cost function may be reduced iteratively, each iteration providing an update of the weight vector w. In the sequel, the iterations for updating the weight vector w are also referred to as optimization steps.

In each optimization step, a first mini-batch may be drawn from the first set of training samples. Herein, a first mini-batch may be a small subset from the first set of training samples. The first mini-batches may be drawn from the first set of training samples randomly and independently of mini-batches of previous optimization steps. Alternatively, first mini-batches may be drawn from the first set of training samples depending on first mini-batches of previous optimization steps.

Similarly, a second mini-batch may be drawn in each optimization step from the first subset of training samples. Herein, a second mini-batch may be a small subset from the first subset of training samples. The second mini-batches may be drawn from the first subset of training samples randomly and independently of mini-batches of previous optimization steps. Alternatively, second mini-batches are drawn from the first subset of training samples depending on second mini-batches of previous optimization steps.

The first and second mini-batches may be used for computing approximate gradients of the first and second parts of the cost function. The approximate gradients may be summed up to obtain an approximate gradient of the cost function, which may be utilized for searching for a minimum of that function.

In another example, the approximate gradient of the second part of the cost function is set to zero when an average prediction performance of the neural network for the second mini-batch is less than or equal to the upper bound for the average prediction performance for the first subset of training samples.

As explained above, the second part of the cost function may be equal to zero when $\overline{A}_2(w)<\varepsilon$, i.e., when the average prediction performance of the neural network for the first subset of training samples is less than or equal to the upper bound $\varepsilon$. The average prediction performance of the neural network for the first subset of training samples may be approximated by the average prediction performance of the neural network for the second mini-batch of training samples. Hence, the approximate second part of the cost function and its gradient with respect to w may be set to zero when the average prediction performance of the neural network for the second mini-batch is less than or equal to the upper bound for the average prediction performance for the first subset of training samples.

In another example, the first part of the cost function further depends on a second subset of training samples from the second set of training samples. In this case, the iteration for reducing the cost function may comprise drawing a third mini-batch from the second subset of training samples and computing an approximate gradient of the first part of the cost function based on the third mini-batch. Furthermore, a cardinality of the third mini-batch divided by a cardinality of the second subset of training samples may be larger than a cardinality of the first mini-batch divided by a cardinality of the first set of training samples.

As explained above, the first part of the cost function may depend on a second subset of training samples from the second set of training samples. When a stochastic optimization method is used for reducing the cost function, a third mini-batch may be drawn from the second subset of training samples in each optimization step. A third mini-batch may be a small subset of the second subset of training samples. The third mini-batches may be drawn from the second subset of training samples randomly and independently of mini-batches of previous optimization steps. Furthermore, the third mini-batches may be drawn from the second subset of training samples independently of the second mini-batches. Alternatively, third mini-batches may be drawn from the second subset of training samples depending on second mini-batches or third mini-batches of previous optimization steps. It is also possible that the second and third mini-batches intersect at one or more training samples. In particular, the second and third mini-batches may be identical.

The cardinality of the first set of training samples may be substantially larger than the cardinality of the second set of training samples. Hence, the cardinality of the first set of training samples may also be substantially larger than the cardinality of the second subset of training samples. To prevent that the first part of the cost function is dominated by the contribution from the first set of training samples, the fraction of the training samples in the third mini-batches relative to the number of training samples in the second subset of training samples may be larger than the fraction of the training samples in the first mini-batches relative to the number of training samples in the first set of training samples. In other words, the cardinality of the third mini-batches divided by the cardinality of the second subset of training samples may be larger than the cardinality of the first mini-batches divided by the cardinality of the first set of training samples. For example, the first and third mini-batches may be drawn in a balanced way from the first set of training samples and the second subset of training samples, respectively, i.e., the first and third mini-batches may contain the same number of training samples.

In another example, the cardinality of the second set of training samples may be increased by selecting a training sample from the second set of training samples, transforming the selected training sample, and including the transformed training sample in the second set of training samples. Thereby, transforming the selected training sample comprises acquiring an image of the selected training sample, transforming the acquired image, generating a feature vector indicative of the transformed image, and adapting a predetermined label of the selected training sample according to the transformation of the acquired image.

As noted above, the feature vector of a training sample may comprise the raw image data. In this case, transforming the selected training sample may comprise transforming the image and adapting the predetermined label of the selected training sample according to the transformation of the image. The transformed training sample may comprise the transformed image as feature vector and the adapted label.

When the feature vector of a training sample comprises features derived from the raw image data, transforming the selected training sample may comprise acquiring the raw image data. Subsequently, the image may be transformed, a feature vector may be derived from the transformed image, and a predetermined label of the selected training sample may be adapted according to the transformation of the image. In this case, the transformed training sample may comprise the feature vector derived from the transformed image and the adapted label.

In both cases, the transformation of the image may comprise, for example, a rotation, a translation, and/or an elastic deformation of one or more objects depicted on the image. Hence, such transformations may be utilized to augment the second set of training samples.

It is emphasized that the invention as described above and in the following does not involve, comprise, or encompass an invasive step, which would represent a substantial physical interference with the body of a patient requiring professional medical expertise to be carried out and entailing a substantial health risk even when carried out with the required professional care and expertise. In particular, the invention does not comprise any surgical or therapeutic activity. Instead, the invention is applicable to any non-invasive medical application and merely relates to a data processing method. For this reason, no surgical or therapeutic activity and, in particular, no surgical or therapeutic step is necessitated or implied by carrying out the invention.

According to the present disclosure, also a data processing system is presented. The data processing system is configured to carry out the steps of any of the methods according to the present invention.

The data processing system may comprise a storage medium for storing the first and second sets of training samples. The data processing system may further comprise a processor such as a micro-processor with one or more processor cores. In addition, the data processing system may comprise a graphics processing unit, which may be used for efficiently computing one or more steps of the method for training the neural network. The data processing system may also comprise communication means such as LAN, WLAN, or cellular communication modems. The data processing system may be connected to one or more servers, which may store training samples, or which may execute one or more steps of the method for training the neural network. Furthermore, the data processing system may comprise peripherals such as screens.

According to the present disclosure, also a computer program is presented, wherein the computer program comprises instructions to cause the data processing system as defined in the independent claims to execute any one of the methods according to the present invention when the computer program is run on the data processing system.

According to the present disclosure, also a computer-readable medium is presented, wherein the computer-readable medium stores the computer program as defined in the independent claims.

It shall be understood that the computer-implemented method for supervised training of an artificial neural network for medical image analysis, the data processing system configured to carry out the steps of the method, the computer program for causing the data processing system to execute the method, and the computer readable medium having stored such computer program have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
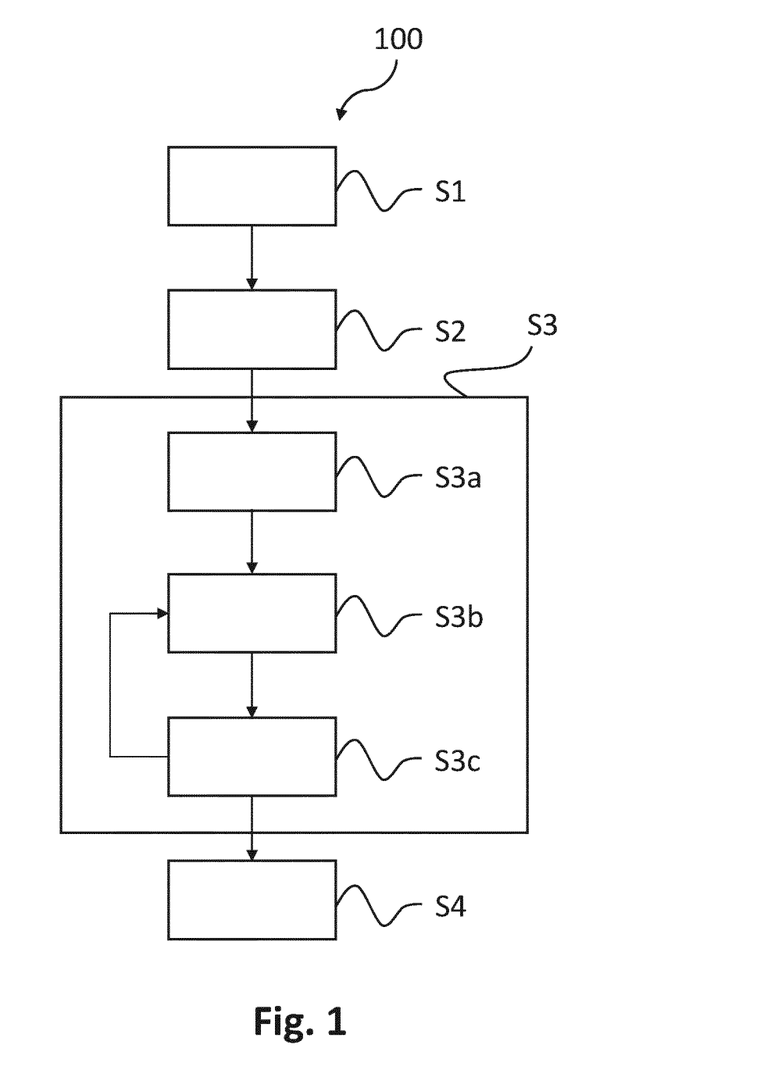
FIG. 1 shows basic steps of an example of a computer-implemented method for training of an artificial neural network for medical image analysis.

FIG. 1 shows basic steps of an example of a computer-implemented method 100 for training of an artificial neural network for medical image analysis. The method 100 comprises the following steps:

In a first step S1, first and second sets of training samples are acquired. Preferably, each training sample of the first and second sets of training samples comprises a feature vector x indicative of a medical image and an associated predetermined label y. The predetermined labels may be determined manually, and may be considered as a ground truth for the training of the neural network. The first and second sets of training samples may be acquired, for example, by loading these sets from a computer readable storage medium or by downloading these sets from a remote server. The average accuracy of the predetermined labels or the confidence in these labels may be better for the second set of training samples than for the first set of training samples.

In a second step S2, an upper bound for the average prediction performance of the neural network for a first subset of training samples is acquired, wherein the first subset of training samples is a subset of the second set of training samples. The average prediction performance of the neural network for the first subset of training samples is preferably the average of label prediction error measures $A_2(y, \hat{y})$ for the first subset of training samples. The upper bound for the average prediction performance of the neural network for the first subset of training samples may be determined intuitively by a user, or it may result from a regulatory specification. For example, the upper bound may be an input provided by a user upon a request from a data processing system. Alternatively, the upper bound may be loaded from a computer readable storage medium, or it may be downloaded from a remote server. It is also possible that the upper bound for the average prediction performance of the neural network for the first subset of training samples is determined automatically or semi-automatically based on a pre-training of the neural network and a subsequent evaluation of the average prediction performance of the pre-trained neural network for the first subset of training samples.

In a third step S3, the neural network is trained. The training of the neural network may comprise reducing or minimizing the cost function $c(w)$, where w denotes the weight vector of the neural network that is to be learned. The cost function is parameterized by training samples and may be expressed as the sum of a first part and a second part. The first part of the cost function depends on the first set of training samples. The first part of the cost function may be or may be based on the average prediction performance of the neural network for the first set of training samples, which may be measured by means of the first label prediction error measure $A_1(y, \hat{y})$. Thus, computing the first part of the cost function may comprise evaluating the first label prediction error measure for the training samples of the first set of training samples and averaging the results.

The second part of the cost function depends on the first subset of training samples. The second part of the cost function may be or may be based on the average prediction performance of the neural network for the first subset of training samples, which may be measured by means of the second label prediction error measure $A_2(y, \hat{y})$. Computing the second part of the cost function may therefore comprise evaluating the second label prediction error measure for the training samples of the first subset of training samples and averaging the results. The second part of the cost function further depends on the upper bound for the average prediction performance of the neural network for the first subset of training samples.

The step S3 may comprise the following steps:

In a step S3a, training parameters such as the weight $\lambda$ may be initialized.

In a step S3b, the cost function $c(w)$ may be reduced for a given weight $\lambda$.

In a step S3c, the average prediction performance $\overline{A}_2(w)$ of the neural network for the first subset of training samples may be determined and compared to a threshold performance. The threshold performance may be equal to or may depend on the upper bound e for the average prediction performance of the neural network for the first subset of training samples. For example, the threshold performance may be a scaled version of the upper bound $\varepsilon$. When the average prediction performance of the neural network for the first subset of training samples is worse than the threshold performance, the weight $\lambda$ may be increased, and the step S3b may be repeated with the increased weight λ. Hence, the weight λ may be increased until the average prediction performance of the neural network for the first subset of training samples is better than the threshold performance. On the other hand, when the average prediction performance of the neural network for the first subset of training samples is better than the threshold performance, the training of the neural network may be finished.

Optionally, in a fourth step S4, the trained neural network may be tested. Thereby, the average prediction performance of the trained neural network may be determined for a set of test samples. Similar to the training samples, each test sample may comprise a feature vector x indicative of a medical image and a predetermined label y. The test samples preferably have accurate predetermined labels y. The average prediction performance of the trained neural network for the set of test samples may be determined, for example, by means of the first or second label prediction error measures.

Figure 2:
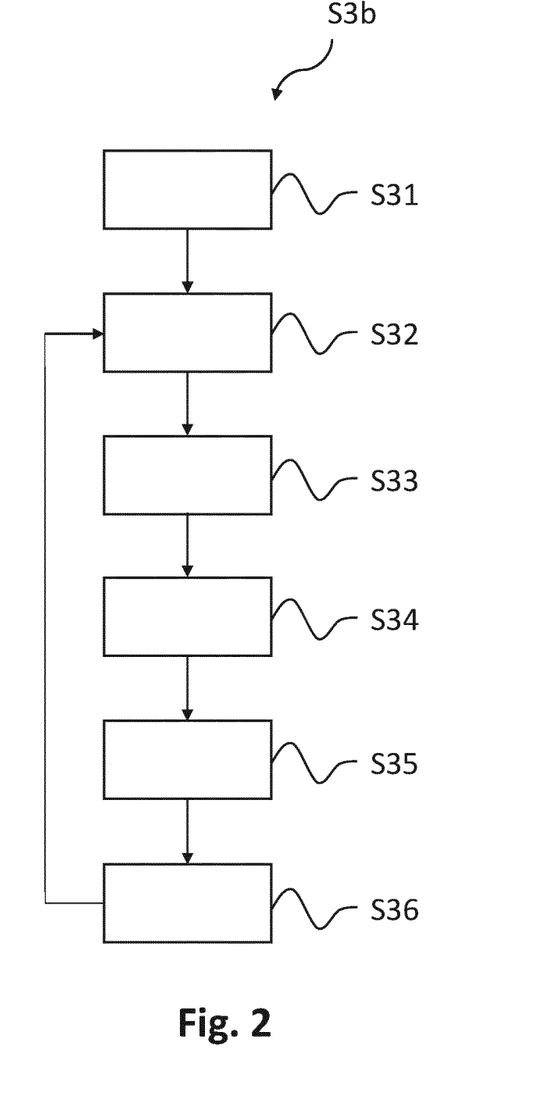
FIG. 2 shows basic steps of an example of a computer-implemented method for reducing the cost function.

FIG. 2 shows basic steps of an example of a computer-implemented method S3b for reducing the cost function.

In step S31, parameters may be initialized. In particular, the weight vector w may be initialized. Furthermore, the value of the cost function for the initial weight vector w may be determined.

In step S32, a first mini-batch may be drawn from the first set of training samples, a second mini-batch may be drawn from the first subset of training samples, and/or a third mini-batch may be drawn from the second subset of training samples, the second subset of training samples being a subset of the second set of training samples.

In step S33, the gradient of the cost function may be computed exactly, or it may be computed approximately based on the first, second, and/or third mini-batches.

In step S34, a step size may be determined. For example, the step size may be determined by means of a back-tracking line search. Numerous other approaches for determining the step size are known from the literature. In a simple approach, the step size may be a scalar, which is reduced successively with each update of the weight vector w.

In step S35, the weight vector w may be updated by performing a step in the gradient descent direction with a step size as determined in step S34.

In step S36, a stopping criterion may be evaluated. For example, the value of the cost function may be computed for the updated weight vector w, and this value of the cost function may be compared to the value of the cost function for the previous weight vector. The reduction of the cost function in the current optimization step may be determined approximately based on the mini-batches determined in step S32. For example, when the reduction of the cost function in the current optimization step does not exceed a predetermined threshold, the method for reducing the cost function may be stopped. Otherwise, another optimization step may be performed by continuing with step S32. In particular, an optimization step preferably comprises the steps S32, S33, S34, S35, and S36, not necessarily in the order as depicted in FIG. 2.

It has to be noted that embodiments of the invention are described with reference to different subject matters. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computer-implemented method for supervised training of an artificial neural network for a medical image analysis, the method comprising:
    acquiring first and second sets of training samples;
    acquiring an upper bound for an average prediction performance of the neural network for a first subset of the second set of training samples; and
    training the neural network by reducing a cost function,
    wherein the training samples comprise feature vectors and associated predetermined labels, the feature vectors being indicative of medical images and the labels pertaining to at least one of anatomy detection, semantic segmentation of medical images, classification of medical images, computer-aided diagnosis, detection and/or localization of biomarkers, and quality assessment of medical images;
    wherein the cost function comprises a first part and a second part;
    wherein the first part of the cost function depends on the first set of training samples;
    wherein the second part of the cost function depends on the first subset of training samples and the upper bound for the average prediction performance of the neural network for the first subset of training samples, and
    wherein the second part of the cost function is configured to prevent the upper bound from exceeding the average prediction performance for the first subset of training samples.

2. The method according to claim 1, wherein an average accuracy of the predetermined labels is better for the second set of training samples than for the first set of training samples.

3. The method according to claim 1, wherein the second part of the cost function depends on a difference between the average prediction performance for the first subset of training samples and the upper bound for the average prediction performance for the first subset of training samples.

4. The method according to claim 3, wherein the second part of the cost function depends on a power of the difference between the average prediction performance for the first subset of training samples and the upper bound for the average prediction performance for the first subset of training samples, the power being strictly greater than one.

5. The method according to claim 1, wherein the second part of the cost function further depends on a positive weight.

6. The method according to claim 5, further comprising:
    increasing the weight upon detecting that the average prediction performance for the first subset of training samples is larger than the upper bound for the average prediction performance for the first subset of training samples.

7. The method according to claim 1, wherein the first part of the cost function is based on a first label prediction error measure;
wherein the second part of the cost function is based on a second label prediction error measure; and
wherein the first and second label prediction error measures are not affine functions of each other.

8. The method according to claim 1, wherein the first part of the cost function further depends on a second subset of training samples from the second set of training samples.

9. The method according to claim 1, wherein the cost function is reduced iteratively;
wherein an iteration comprises drawing a first mini-batch from the first set of training samples and computing an approximate gradient of the first part of the cost function based on the first mini-batch; and/or
wherein the iteration comprises drawing a second mini-batch from the first subset of training samples and computing an approximate gradient of the second part of the cost function based on the second mini-batch.

10. The method according to claim 9, wherein the approximate gradient of the second part of the cost function is set to zero when an average prediction performance of the neural network for the second mini-batch is less than or equal to the upper bound for the average prediction performance for the first subset of training samples.

11. The method according to claim 9,
wherein the first part of the cost function further depends on a second subset of training samples from the second set of training samples;
wherein the iteration comprises drawing a third mini-batch from the second subset of training samples, and computing an approximate gradient of the first part of the cost function based on the third mini-batch; and
wherein a cardinality of the third mini-batch divided by a cardinality of the second subset of training samples is larger than the cardinality of the first mini-batch divided by the cardinality of the first set of training samples.

12. The method according to claim 1, further comprising:
increasing a cardinality of the second set of training samples by selecting a training sample from the second set of training samples, transforming the selected training sample, and including the transformed training sample in the second set of training samples,
wherein transforming the selected training sample comprises acquiring an image of the selected training sample, transforming the acquired image, generating a feature vector indicative of the transformed image, and adapting a predetermined label of the selected training sample according to the transformation of the acquired image.

13. A system for supervised training of an artificial neural network for a medical image analysis, comprising:
a memory that stores a plurality of instructions; and
processor circuitry that couples to the memory and is configured to execute the plurality of instructions to:
acquire first and second sets of training samples;
acquire an upper bound for an average prediction performance of the neural network for a first subset of the second set of training samples; and
train the neural network by reducing a cost function,
wherein the training samples comprise feature vectors and associated predetermined labels, the feature vectors being indicative of medical images and the labels pertaining to at least one of anatomy detection, semantic segmentation of medical images, classification of medical images, computer-aided diagnosis, detection and/or localization of biomarkers, and quality assessment of medical images;
wherein the cost function comprises a first part and a second part;
wherein the first part of the cost function depends on the first set of training samples;
wherein the second part of the cost function depends on the first subset of training samples and the upper bound for the average prediction performance of the neural network for the first subset of training samples, and
wherein the second part of the cost function is configured to prevent the upper bound from exceeding the average prediction performance for the first subset of training samples.

14. A non-transitory computer-readable medium for storing executable instructions, which cause a method to be performed for supervised training of an artificial neural network for a medical image analysis, the method comprising:
acquiring first and second sets of training samples;
acquiring an upper bound for an average prediction performance of the neural network for a first subset of the second set of training samples; and
training the neural network by reducing a cost function,
wherein the training samples comprise feature vectors and associated predetermined labels, the feature vectors being indicative of medical images and the labels pertaining to at least one of anatomy detection, semantic segmentation of medical images, classification of medical images, computer-aided diagnosis, detection and/or localization of biomarkers, and quality assessment of medical images;
wherein the cost function comprises a first part and a second part;
wherein the first part of the cost function depends on the first set of training samples;
wherein the second part of the cost function depends on the first subset of training samples and the upper bound for the average prediction performance of the neural network for the first subset of training samples, and
wherein the second part of the cost function is configured to prevent the upper bound from exceeding the average prediction performance for the first subset of training samples.

* * * * *